(12) United States Patent
Quijano et al.

(10) Patent No.: US 6,685,702 B2
(45) Date of Patent: Feb. 3, 2004

(54) DEVICE FOR TREATING TISSUE AND METHODS THEREOF

(76) Inventors: Rodolfo C. Quijano, 27451 Lost Trail La., Laguna Hills, CA (US) 92653; Hosheng Tu, 15 Riez, Newport Coast, CA (US) 92657

( * ) Notice: Subject to any disclaimer, the term of this patent is extended or adjusted under 35 U.S.C. 154(b) by 198 days.

(21) Appl. No.: 09/900,586

(22) Filed: Jul. 6, 2001

(65) Prior Publication Data

US 2003/0014098 A1 Jan. 16, 2003

(51) Int. Cl.[7] .............................................. A61B 18/14
(52) U.S. Cl. .......................... 606/41; 606/20; 606/21; 606/28
(58) Field of Search ............................. 606/20, 21, 27, 606/28, 33, 41, 49

(56) References Cited

U.S. PATENT DOCUMENTS

| | | | |
|---|---|---|---|
| 4,860,744 A | 8/1989 | Johnson et al. | |
| 5,348,554 A | 9/1994 | Imran et al. | |
| 5,522,815 A | 6/1996 | Durgin, Jr. et al. | |
| 5,529,067 A | 6/1996 | Larsen et al. | |
| 5,733,280 A * | 3/1998 | Avitall ........................ | 606/21 |
| 5,755,663 A | 5/1998 | Larsen et al. | |
| 5,967,976 A | 10/1999 | Larsen et al. | |
| 6,015,407 A | 1/2000 | Rieb et al. | |
| 6,056,745 A * | 5/2000 | Panescu et al. ............... | 606/41 |
| 6,106,521 A | 8/2000 | Blewett et al. | |
| 6,113,593 A | 9/2000 | Tu et al. | |
| 6,212,433 B1 | 4/2001 | Behl | |
| 6,235,021 B1 | 5/2001 | Sieben | |
| 6,238,393 B1 | 5/2001 | Mulier et al. | |
| 6,241,666 B1 | 6/2001 | Pomeranz et al. | |
| 6,379,348 B1 * | 4/2002 | Onik ........................... | 606/21 |
| 6,451,011 B2 * | 9/2002 | Tu ............................... | 606/21 |

FOREIGN PATENT DOCUMENTS

WO     WO 98/19595     5/1998

* cited by examiner

*Primary Examiner*—Lee Cohen

(57) ABSTRACT

A method and devices for treating a target tissue comprising providing thermal energy to the target tissue and simultaneously providing cryogenic energy to peripheral tissue adjacent or surrounding said target tissue adapted for shielding the peripheral tissue from any adverse effect of the thermal energy. The cooling may be accomplished with a cryogenic arrangement comprising two elements of different electromotive potential conductively connected at a probe junction, and passing an electrical current through the elements to reduce a temperature of the probe junction in accordance with the Peltier effect.

19 Claims, 6 Drawing Sheets

DEVICE FOR TREATING TISSUE AND METHODS THEREOF

FIELD OF THE INVENTION

The present invention relates generally to a medical device for treating tissue and methods of use, and more particularly, to a medical device and methods for radiofrequency thermal ablation which is provided with a controlled cooling means according to the Peltier effect for effectively creating a large lesion.

BACKGROUND OF THE INVENTION

This invention relates to an electrode element assembly for treating a target tissue by providing thermal energy to the target tissue while simultaneously providing cryogenic energy to the peripheral tissue adjacent or surrounding the target tissue adapted for shielding the peripheral tissue from the effect of thermal therapy.

Generally, thermal energy could be clinically applied to treat tissue, such as tumor, cancerous tissue, prostate, arrhythmia, atrial fibrillation and the like. However, difficulties have been encountered for a device system to provide highly controlled, localized heat to a precise point or region within a patient's body that causes little effects to the peripheral tissue adjacent, encircling, or surrounding the target tissue.

In a patient's heart, supraventricular tachycardia, ventricular tachycardia, and atrial fibrillation are conditions collectively known as arrhythmias. During an arrhythmia, abnormal electrical signals are generated in about the endocardial tissue which cause irregular beating of the heart. One method used to treat these arrhythmias involves creating lesions within the chambers of the heart or the pulmonary veins. These lesions are intended to halt the passage of the abnormal currents through the heart. A radiofrequency catheter has been routinely used to ablate the aberrant electrical activity. Increasing the radiofrequency power to a catheter in an attempt to increase the size of the lesions has caused degradation of the blood in the region where ablation is taking place.

U.S. Pat. No. 5,348,554 to Imran et al. discloses a catheter system with a cooled electrode. Specifically, an electrode having a chamber therein is provided with a circulated cooling liquid to cool the electrode. U.S. Pat. No. 6,241,666 to Pomeranz et al., and U.S. Pat. No. 6,015,407 to Rieb et al. also disclose a catheter system with a modified cooled electrode, mostly with a liquid coolant arrangement that is bulky, expensive or poses unnecessary risk to a patient. The entire contents of the above-cited patents are incorporated herein by reference.

A radiofrequency catheter with a liquid-cooled electrode includes extra auxiliary equipments, such as a circulating pump, a cooling liquid source, control instruments, and accessories. As disclosed in U.S. Pat. No. 5,348,554, the cooled liquid is intended to cool the inner chamber of the tip electrode. However, the temperature of the outer surface of the electrode may rise to an unacceptable level resulting in tissue degradation, blood clot, or coagulation. As is well known to an ordinary technician skilled in the art that the resistive heat of radiofrequency ablation comes from the tissue-electrode contact surface. In an example of U.S. Pat. No. 5,348,554, a portion of the isotherm G showed in FIG. 18 is in the blood-contacting region. Even with a liquid-cooled setup thereof, the isotherm temperature of the isotherm G might reach as high as 66.633° C. which is far above the cell necrosis temperature.

Therefore, there is an urgent clinical need for providing a medical device and methods for treating a target tissue comprising providing thermal energy to the target tissue and simultaneously or subsequently providing cryogenic energy to the peripheral tissue adjacent or surrounding the target tissue adapted for shielding the peripheral tissue from any detrimental effects of the thermal energy, if any.

Johnson et al. in U.S. Pat. No. 4,860,744 discloses a thermoelectrically controlled heat medical catheter, which is incorporated herein by reference. More particularly, Johnson et al. discloses a system and methods for providing controlled heating or cooling of a small region of body tissue to effectuate the removal of tumors and deposits, such as atheromatous plaque. Though Johnson et al. teaches a medical catheter in accordance with the Peltier effect adapted for thermoelectric heating/cooling for destruction of diseased tissue and/or tumors in various parts of the body, Johnson et al. does not disclose a method for cooling the peripheral tissue so as to focus the therapeutically thermal energy to the target tissue alone.

Larsen et al. in U.S. Pat. Nos. 5,529,067, 5,755,663, and 5,967,976 disclose methods and apparatus for use in procedures related to the electrophysiology of the heart, such as identifying or evaluating the electrical activity of the heart, diagnosing and/or treating conditions associated with the electrophysiology of the heart, entire contents of which are incorporated herein by reference. Specifically, Larsen et al. teaches an apparatus having thermocouple elements of different electromotive potential conductively connected at a junction and reducing the temperature of the junction in accordance with the Peltier effect for cooling the contacted heart tissue. However, Larsen et al. does not teach a method for treating a target tissue comprising providing thermal energy to the target tissue and simultaneously or subsequently providing cryogenic energy to the peripheral tissue adjacent or surrounding the target tissue adapted for shielding the peripheral tissue from any adverse effect of the thermal energy.

SUMMARY OF THE INVENTION

In general, it is an object of the present invention to provide a device and a method for treating a target tissue, the method comprising providing thermal energy to the target tissue and providing cryogenic energy to peripheral tissue adjacent or surrounding said target tissue adapted for shielding the peripheral tissue from any adverse effect of the thermal energy. The cryogenic energy provided for the peripheral tissue may be provided simultaneously, subsequently or in a pre-programmed mode with respect to the thermal therapy at no higher than 37° C. and is compatible with the tissue viability or functionality.

In one embodiment, the method of cooling may be provided by a probe junction, the probe junction being conductively connected to two elements of different electromotive potential and electrical current being passed through the elements to reduce temperature of the probe junction in accordance with the Peltier effect and thereby cool the peripheral tissue adjacent or surrounding the target tissue.

In another embodiment, the target tissue may be selected from a group consisting of tumor, cancerous tissue, arrhythmia, pulmonary vein, benign prostate hyperplasia, breast tumor, breast cancer, inflammation, atherosclerosis, vulnerable plaque, or the like. The thermal energy may be selected from a group consisting of radiofrequency energy, microwave energy, laser energy, ultrasound energy, and combination thereof.

It is another object of the present invention to provide an electrode element assembly comprising a metallic tip electrode, means for delivering current to the metallic tip electrode, elements of different electromotive potential conductively connected at a probe junction, wherein the probe junction surrounds at least a portion of periphery of the metallic tip electrode, and means for passing an electrical current through said elements to reduce temperature of said probe junction in accordance with the Peltier effect.

In still another embodiment, the probe junction may form a complete circle or circular-like configuration that surrounds the periphery of the tip electrode. The probe junction may optionally be permeably porous for fluid or particles passage. The electrode assembly is configured so as the metallic tip electrode being adapted for intimately contacting the tissue to be treated and the probe junction being adapted for not contacting the tissue to be treated. The metallic tip electrode may further comprise at least a needle or probe configured for penetrating into the tissue to be treated.

It is still another object of the present invention to provide an apparatus for treating tissue comprising at least one electrode assembly, wherein said electrode assembly comprises a metallic tip electrode; means for delivering current to the metallic tip electrode; elements of different electromotive potential conductively connected at a probe junction, wherein the probe junction surrounds at least a portion of periphery of the metallic tip electrode; and means for passing an electrical current through said elements to reduce temperature of the probe junction in accordance with the Peltier effect and thereby cool tissue adjacent the treated tissue. The apparatus may be a catheter, a probe, a cannula, or an endoscopic instrument.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 6, what is shown is an embodiment of a medical device having site-specific therapeutic ability and capability comprising thermally treating a target tissue while providing cryogenic energy to peripheral tissue adjacent to or surrounding the target tissue adapted for shielding the peripheral tissue from any adverse effect of the thermal energy. The cryogenic energy may be provided sufficiently to neutralize the adverse effect of the thermal energy.

Figure 1:
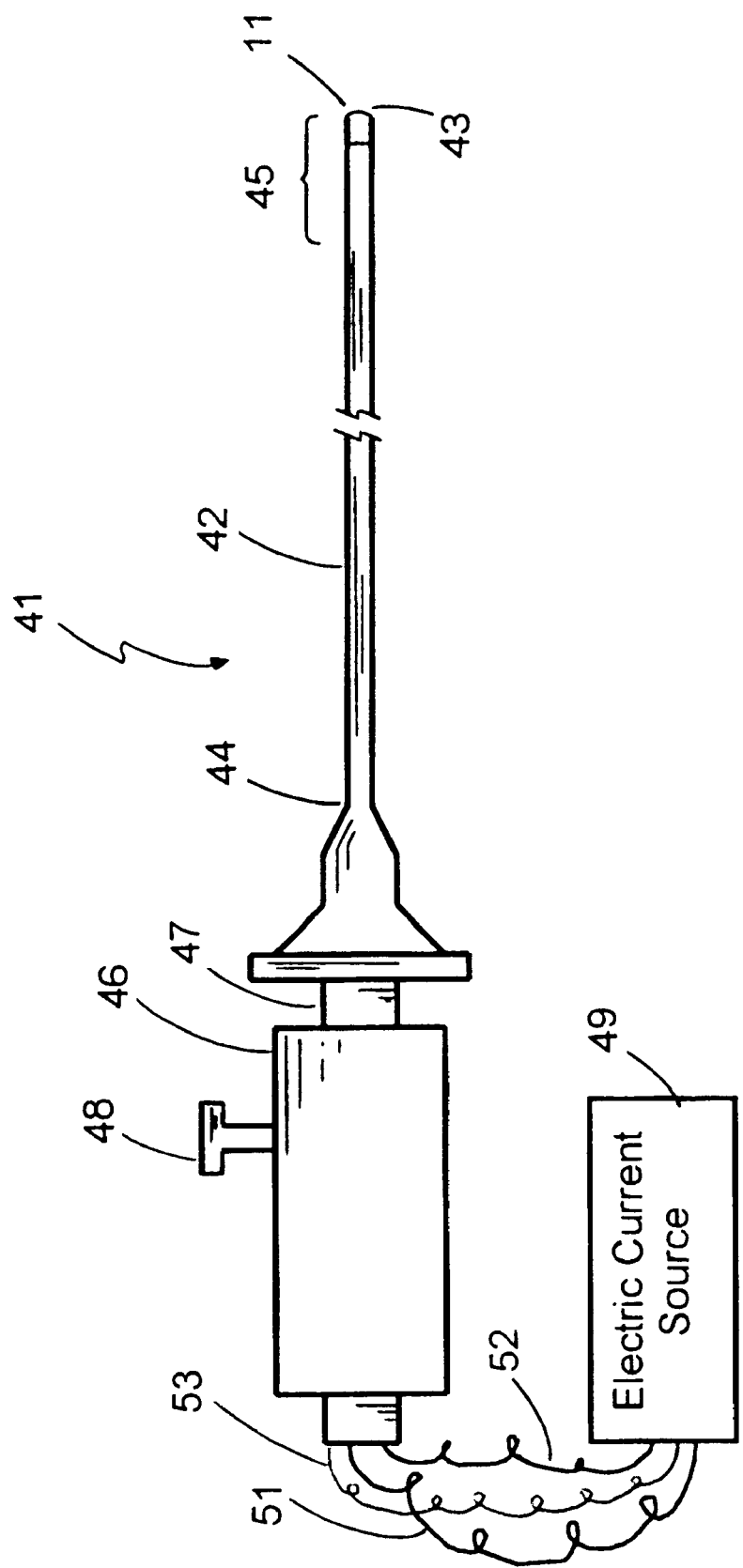
FIG. 1 is an overall view of a medical apparatus constructed in accordance with the principles of the present invention.

FIG. 1 shows an overall view of a medical apparatus constructed in accordance with the principles of the present invention. The medical apparatus of the present invention may comprise a catheter, a probe, a cannula, an endoscopic instrument, or the like that is suitable for the intended applications in treating tumor, cancerous tissue, arrhythmia, pulmonary vein, benign prostate hyperplasia, breast tumor, breast cancer, inflammation, atherosclerosis, vulnerable plaque, or the like.

In one embodiment, the medical catheter 41 comprises a flexible catheter body 42 having a distal end 43, a proximal end 44 and a distal section 45. A handle 46 is attached to the proximal end 44 of the catheter body. The catheter may be provided with an external electric current source 49 and two insulated conducting wires 51 and 52 for providing electrical current to an electrode assembly 11 (heated or cooled) at the catheter distal section 45. The electric current source 49 may be a high frequency current source, for example radiofrequency current or ultrasound frequency current.

The catheter may also comprise a steerable mechanism 47 for steering the distal section 45 into a body conduit and also steering the electrode assembly 11 at the distal section firmly against the target tissue for treatment. A power switch control arrangement 48 may be provided to control the electrical current, the current flow direction, and other operating conditions. In a preferred embodiment, the electrical conductor 53 is to provide an electrical current to the tip electrode 12 or equivalent for thermal energy therapy.

Figure 2:
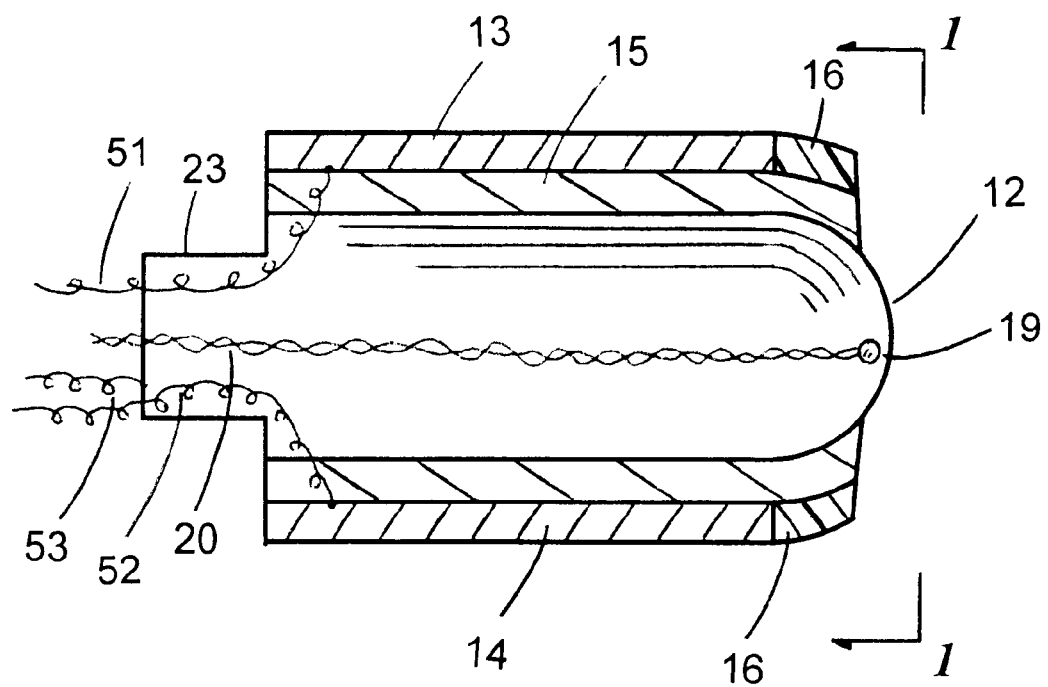
FIG. 2 is a cross-sectional view of the electrode assembly of the medical apparatus, showing a tip electrode and two elements of different electromotive potential conductively connected at a probe junction.

FIG. 2 shows a cross-sectional view of the electrode assembly 11 of the medical apparatus of the present invention, showing a tip electrode 12 and two elements 13, 14 of different electromotive potential conductively connected at a probe junction 16. The "probe junction" of the present invention is intended to mean a junction with a somewhat curved configuration to provide cryogenic energy around or surround the tip electrode or equivalent adapted for shielding the peripheral tissue from any adverse effect of the thermal energy. Further, the probe junction may be selected from a group consisting of circular, semi-circular, rounded, oval, random curved shape or other suitable configuration.

According to the principles of the present invention, the electrode assembly 11 may comprise a metallic tip electrode 12 and means for delivering current 53 to the metallic tip electrode; The electrode assembly further comprises two elements 13, 14 of different electromotive potential conductively connected at a probe junction 16, wherein the probe junction 16 is configured to surround at least a portion of periphery (outer surface) of the metallic tip electrode 12 and means 51, 52 for passing an electrical current through the two elements 13, 14 to reduce temperature of the probe junction 16 in accordance with the Peltier effect.

Optionally, a temperature sensor 19 may be secured at about the tip electrode 12 for monitoring the tissue temperature, wherein the measured temperature is relayed through a temperature sensing wire 20 to a monitor or to a closed-loop temperature controller 26 for controlling the thermal energy supply.

Figure 3:
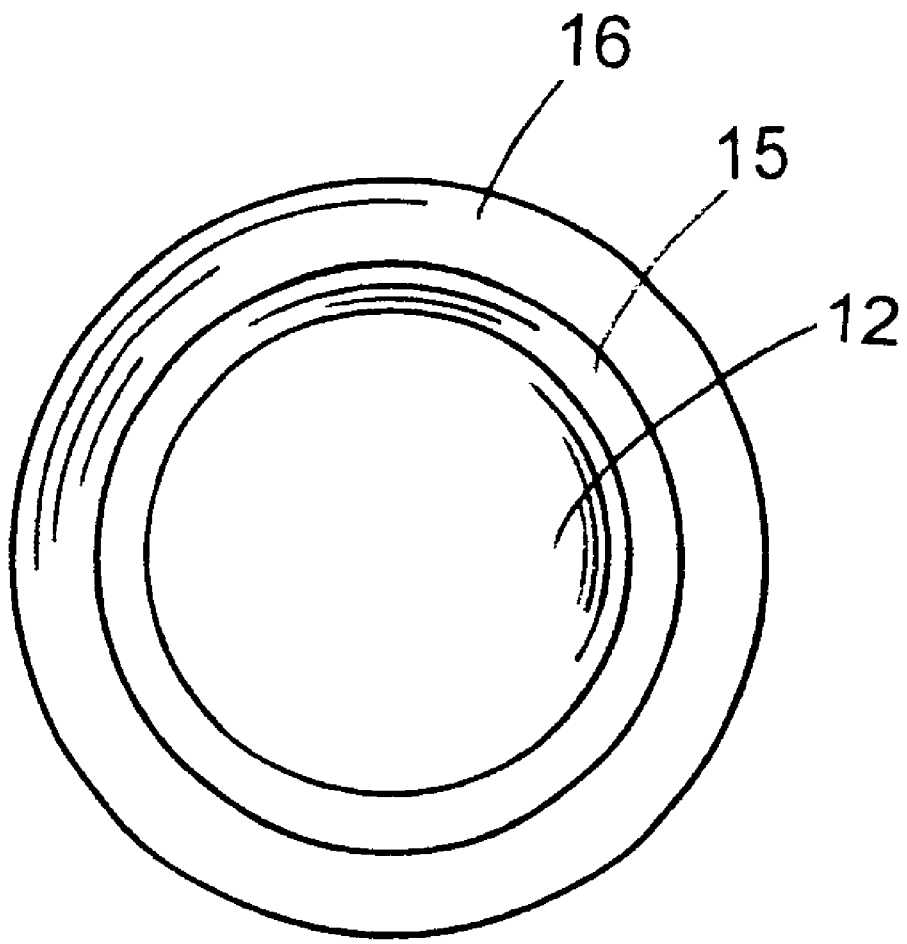
FIG. 3 is a transverse cross-sectional view of the electrode assembly, section 1—1 of FIG. 2.

FIG. 3 shows a transverse cross-sectional view of the electrode assembly 11, section 1—1 of FIG. 2. Between the probe junction 16 and the tip electrode 12, there provided an electrically insulated layer or buffer zone 15 to separate the tip electrode 12 from the probe junction 16 (also known as the cooling junction in one case). In an alternate embodiment, the tip electrode may also comprise an arrangement suitable for providing the thermal therapy selected from a group consisting of microwave energy, ultrasound energy, radiofrequency energy, laser energy, infrared energy, near infrared, ultraviolet, or the like.

Figure 4:
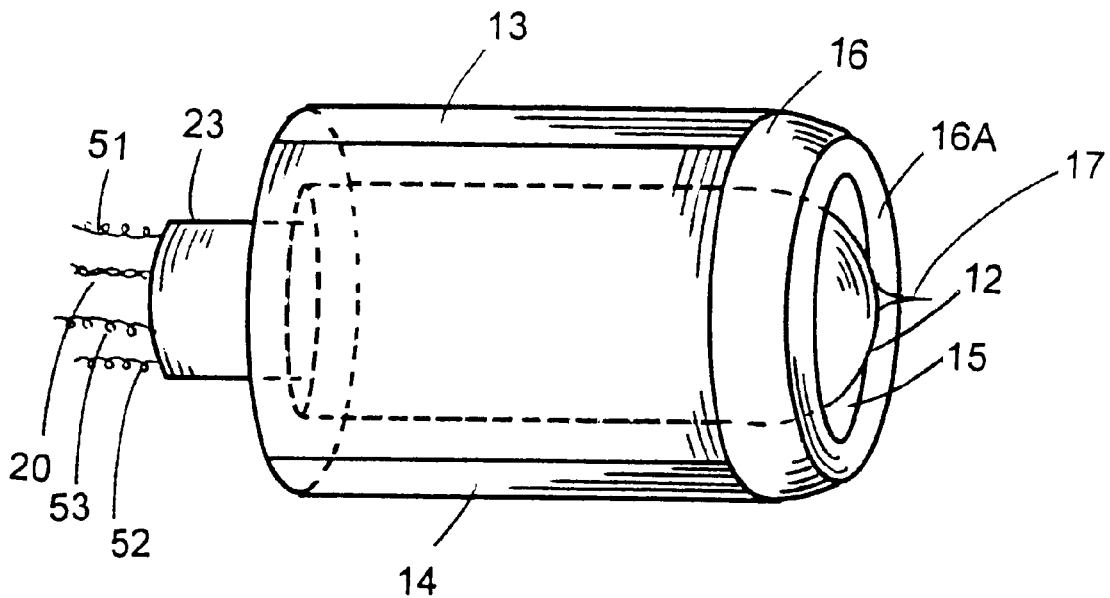
FIG. 4 is a perspective view of the electrode assembly of the present invention.

FIG. 4 shows a perspective view of the electrode assembly 11 of the present invention. The tip electrode 12 is separated by a buffer layer or zone 15 from the junction 16. The electrode assembly has a stem 23 to be secured to the tip or side section of a medical apparatus, such as a catheter or an endoscopic instrument. The electrode assembly 11 of the present invention is generally configured so as the metallic tip electrode being adapted for intimately contacting the tissue to be treated and the probe junction being adapted for not contacting the tissue to be treated. The tip electrode 12 may comprise at least a needle 17 or probe configured for penetrating into the tissue to be treated.

Blewett et al. in U.S. Pat. No. 6,106,521 discloses an apparatus with a needle like probe for thermal treatment of tissue. Behl in U.S. Pat. No. 6,212,433 discloses a system for treating a target tissue beneath a tissue surface by deploying a needle like electrode array. Durgin, Jr. et al. in U.S. Pat. No. 5,522,815 discloses an integrated catheter with a needle for diverse in situ tissue therapy. Mulier et al. in U.S. Pat. No. 6,238,393 discloses an apparatus for creating a bi-polar virtual electrode through a needle like inner electrode. The contents of the above-cited patents are incorporated herein by reference. A needle or needle like electrode for penetrating into a tissue is well known to one ordinary artisan skilled in the art of electrode ablation.

As described in U.S. Pat. Nos. 4,860,744, 5,529,067 and generally shown in FIG. 5 of the present invention, general principles of the Peltier effect are illustrated below as an example. The therapeutic element 81 utilizes one pair of P (positive) and N (negative) thermoelectric elements or legs. The materials of the thermoelectric therapeutic element 81 may be configured in a variety of different ways such as bar or wire forms design. The P leg 82 and N leg 83 are electrically separated along their lengths, but are conductively joined at one end. The contact junctions 86, 87 represent one of junctions. With reference to U.S. Pat. No. 4,860,744, a molybdenum silicide plate to join the two legs at the contact junctions 86, 87 may be optionally used. The molybdenum silicide plate that connects the legs at the contact junction 86, 87 is referred to as a cool junction "shoe" 80 (can be a hot junction shoe if the current is reversed). The P and N legs are separately connected at a second end to connector wires 84, 85. The ends of the thermoelectric elements are referred as junctions. The other set of junctions are the reference junctions 89, 90. The manner in which P and N legs are formed and the Peltier effects is known to those skilled in the art and forms no part of the present invention.

Figure 5:
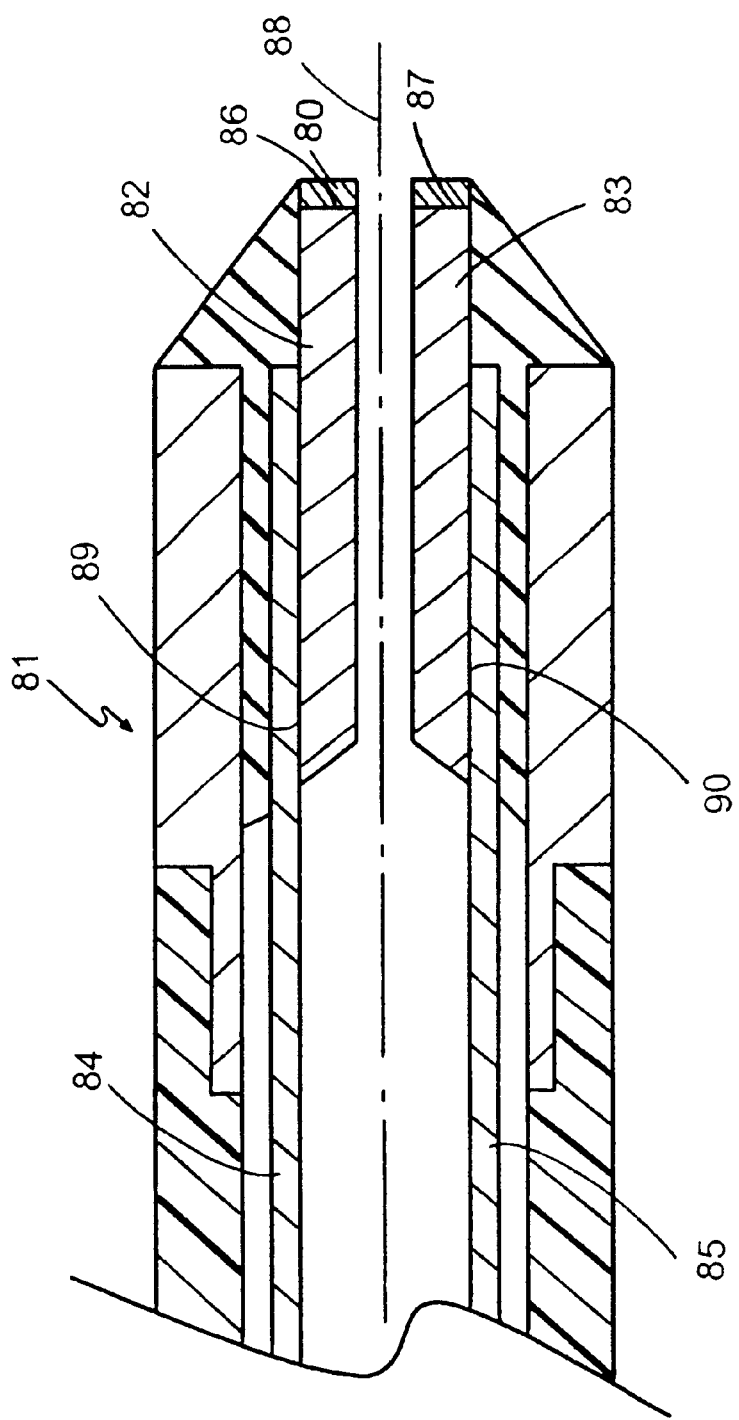
FIG. 5 is a longitudinal cross-sectional view of the distal end portion of a typical apparatus utilizing the Peltier effect as an example.

Referring to FIG. 5, thermoelectric cooling of the contact junctions 86, 87 occurs when an electrical current is passed through the legs in the N to P direction, which is controlled by the power switch control 48 at the handle 46. The reference junctions 89, 90 experience heating when this electrical current is passed through the legs. Additional Joulean heating occurs in the legs 82, 83 because of the internal electrical resistance of the legs. This Joulean heating diminishes the cooling of the cold junction shoe 80. There is a need to disperse the heat generated at the legs and at the reference junctions 89, 90.

Figure 6:
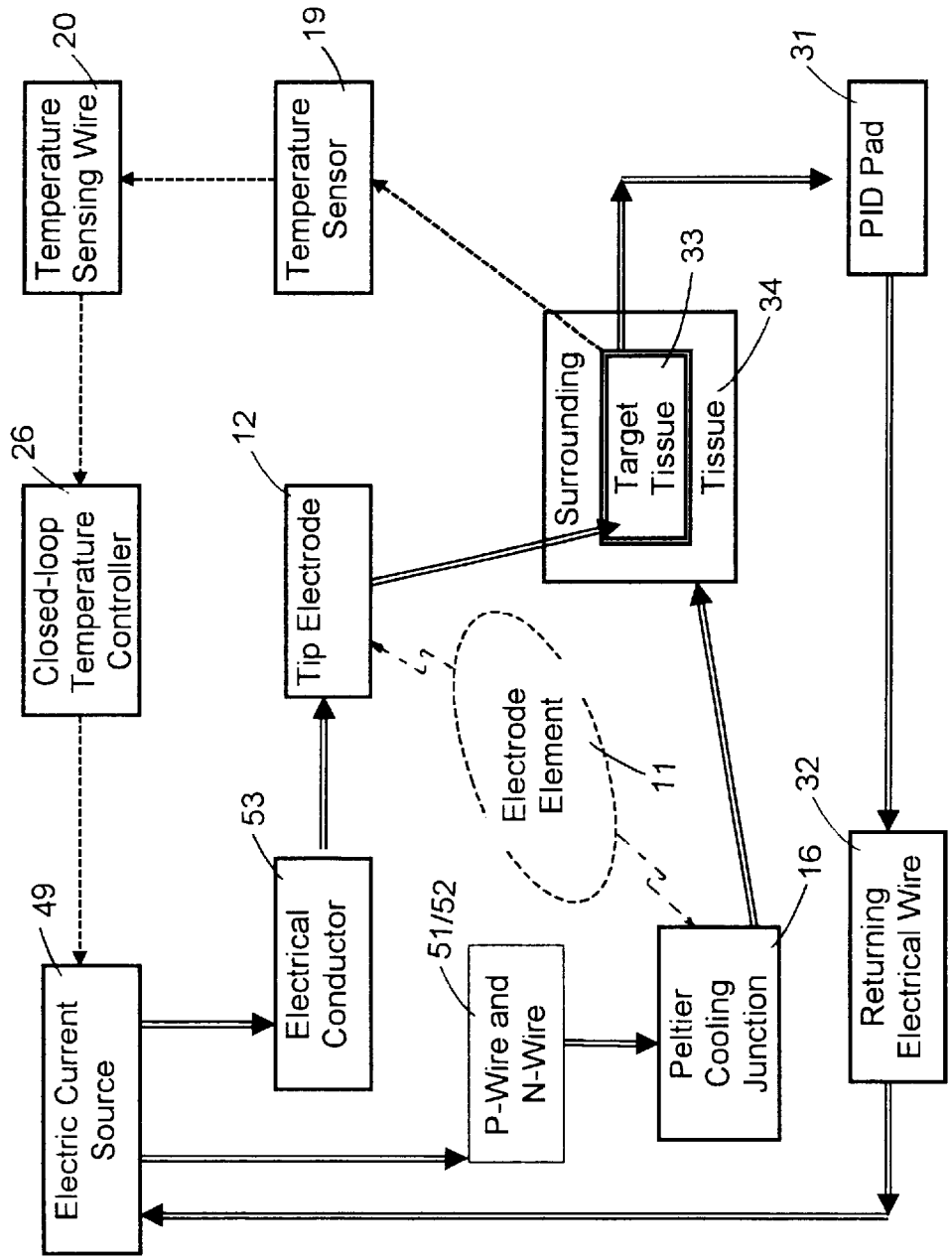
FIG. 6 is a schematic diagram illustrating the methods for providing thermal energy to the target tissue and providing cryogenic energy to peripheral tissue adjacent or surrounding said target tissue adapted for shielding the peripheral tissue from an adverse effect of the thermal energy.

FIG. 6 shows a schematic diagram illustrating the methods for providing thermal energy to the target tissue 33 and providing cryogenic energy to peripheral tissue 34 adjacent or surrounding said target tissue adapted for shielding the peripheral tissue from any adverse effect of the thermal energy. The mode of operating heating and cooling of the present invention may be simultaneous, alternate, sequential or other pre-programmed mode. In one embodiment of radiofrequency ablation, the radiofrequency current is passed from a patient through a PID pad 31 and a returning electrical wire 32 and returned to the radiofrequency generator for a complete current circuit.

As referred to FIG. 2 of the present invention, the tip electrode 12 is configured to be positioned for contacting the target tissue intimately. More particularly, the tip electrode 12 may be configured as a concave configuration adapted for encircling the tissue, such as a tumor or polyp, for purposes of intimate contact. Depending on the shape and structure of the target tissue, other configuration for the tip electrode may also be applicable, such as convex, semi-cylindrical, circular, elliptic hyperboloid, ellipsoid, oblate spheroid, hyperbolic paraboloid, elliptic paraboloid, and irregular configuration.

As shown in FIGS. 1 and 4, the electromotive elements 13 and 14 are configured and arranged so that the reference junctions are adjacent a surface of the catheter body 42. By such an arrangement, the heat generated at the reference junctions is constantly swept away by the flowing blood stream. Therefore, the probe junction 16 can maintain its coolness effective for neutralizing the heat generated at the ablation tip electrode 12. In a certain embodiment, the probe junction 16 may preferably be configured permeably porous for fluid or small particles, such as blood cells, to flow through. The flow-through blood stream may enhance the heat dissipation via convection. In another embodiment, the probe junction is impermeable to any fluid or particles.

Though the medical apparatus system of the present invention is described to apply thermal energy through a tip electrode arrangement surrounded by a cooling probe junction, the reverse arrangement for treating a target tissue by comprising providing cryogenic energy to the target tissue and providing moderate thermal energy to peripheral tissue adjacent or surrounding the target tissue adapted for shielding the peripheral tissue from any adverse effect of the cryogenic therapy is also equally applicable in the present invention. In an alternate embodiment, an electrode assembly may comprise two elements of different electromotive potential conductively connected at a probe junction; means for passing an electrical current through said elements to reduce temperature of said probe junction in accordance with the Peltier effect; a metallic hollow electrode, wherein said hollow electrode surrounds at least a portion of the probe junction; and means for delivering current to the metallic hollow electrode.

From the foregoing description, it should now be appreciated that a medical apparatus and methods comprising incorporating thermal therapy and cryogenic energy sufficiently to treat tissue providing thermal energy to the target tissue and providing cryogenic energy to peripheral tissue adjacent or surrounding the target tissue adapted for shielding the peripheral tissue from any effect of said thermal energy has been disclosed. While the invention has been described with reference to a specific embodiment, the description is illustrative of the invention and is not to be construed as limiting the invention. Various modifications and applications may occur to those who are skilled in the art, without departing from the true spirit and scope of the provisional application.

What is claimed is:

1. An electrode assembly comprising:

a metallic tip electrode;

means for delivering current to the metallic tip electrode;

elements of different electromotive potential conductively connected at a probe junction, wherein said probe junction sounds at least a portion of periphery of the metallic tip electrode; and means for passing an electrical current through said elements to reduce temperature of said probe junction in accordance with the Peltier effect, wherein the temperature of said probe junction is lower than a temperature of said electrode.

2. The electrode assembly of claim 1, wherein said probe junction forms a complete circle surrounding the periphery of said tip electrode.

3. The electrode assembly of claim 1, wherein the probe junction is permeably porous.

4. The electrode assembly of claim 1, wherein said electrode assembly is securely mounted at a distal section o an apparatus for treating tissue, said apparatus being a catheter or an endoscopic instrument.

5. The electrode assembly of claim 1, wherein the electrode assembly is configured so as the metallic tip electrode being adapted for intimately contacting the tissue to be treated and the probe junction being adapted for not contacting the tissue to be treated.

6. The electrode assembly of claim 1, wherein the metallic tip electrode further comprises at least a needle or probe configured for penetrating into the tissue to be treated.

7. The electrode assembly of claim 1, wherein the current is high frequency current.

8. A method for treating a target tissue, the method comprising providing thermal energy to the target tissue and providing cryogenic energy to peripheral tissue adjacent or surrounding said target tissue adapted for shielding the peripheral tissue from an adverse effect of said thermal energy, wherein the cryogenic energy is provided by a probe junction, said probe junction being conductively connected to two elements of different electromotive potential and electrical current being passed through said elements to reduce temperature of said probe junction in accordance with Peltier effect and thereby cool said peripheral tissue.

9. The method for treating a target tissue of claim 8, wherein the target tissue is a tumor or a cancerous tissue.

10. The method for treating a target tissue of claim 8, wherein the target tissue is an arrhythmia.

11. The method for treating a target tissue of claim 8, wherein the thermal energy is radiofrequency energy.

12. The method for treating a target tissue of claim 11, wherein the target tissue is a pulmonary vein.

13. The method for treating a target tissue of claim 8, wherein the thermal energy is microwave energy or laser energy.

14. The method for treating a target tissue of claim 8, wherein the thermal energy is ultrasound energy.

15. The method for treating a target tissue of claim 8, wherein the target tissue is a breast tumor or breast cancer.

16. The method for treating a target tissue of claim 8, the method further comprising monitoring temperature of the target tissue in accordance with thermocouple principles.

17. The method for treating a target tissue of claim 8, wherein the temperature for the peripheral tissue adjacent or surrounding said target tissue is maintained at below 37° C.

18. The method for treating a target tissue of claim 10, the method further comprising detecting said arrhythmia prior to treatment.

19. The method for treating a target tissue of claim 8, wherein the target tissue is benign prostate hyperplasia.

* * * * *